United States Patent
Yavitz

Patent Number: 5,462,049
Date of Patent: Oct. 31, 1995

[54] INTRAORAL SMOKE REMOVAL DEVICE

[76] Inventor: Edward Q. Yavitz, 3828 Spring Creek Rd., Rockford, Ill. 61114

[21] Appl. No.: 254,990

[22] Filed: Jun. 7, 1994

[51] Int. Cl.$^6$ .................. A62B 7/10; A62B 23/02; A61C 3/00

[52] U.S. Cl. .................. 128/205.27; 128/207.14; 128/205.29; 128/863; 433/215; 433/229

[58] Field of Search ............... 128/201.13, 204.13, 128/205.27–205.29, 206.29, 863, 207.14; 433/215, 229

[56] References Cited

U.S. PATENT DOCUMENTS

| | | | |
|---|---|---|---|
| 704,017 | 7/1992 | Fowler | 128/205.29 |
| 712,304 | 10/1902 | Jacobs et al. | 128/204.13 |
| 893,213 | 7/1908 | Whiteway | 128/206.29 |
| 3,774,601 | 11/1973 | Langone | 128/205.29 |
| 3,795,744 | 3/1974 | Ogawa et al. | 426/3 |
| 4,071,026 | 1/1978 | Bevins | 128/205.29 |
| 4,388,328 | 6/1983 | Glass | 426/3 |
| 4,485,118 | 11/1984 | Carroll et al. | 426/5 |
| 4,861,268 | 8/1989 | Garay et al. | 433/229 |
| 5,052,410 | 10/1991 | Stubbs | 128/859 |
| 5,194,003 | 3/1993 | Garey et al. | 433/215 |

*Primary Examiner*—Kimberly L. Asher
*Attorney, Agent, or Firm*—Foley & Lardner

[57] ABSTRACT

The present invention is directed to an intraoral device for absorbing tar and nicotine normally inhaled by a smoker. The device includes a flexible pad which is disposed within the mouth of a wearer. A plurality of tar and nicotine absorbent particles are embedded in the flexible pad. Often, a retainer portion is attached to the flexible pad to engage the teeth of the wearer for holding the flexible pad in a desired position within the wearer's mouth. Preferably, the pad will be held along the palate of the wearer. Additionally, the flexible pad may also be impregnated with a breath freshener.

20 Claims, 1 Drawing Sheet

INTRAORAL SMOKE REMOVAL DEVICE

FIELD OF THE INVENTION

The present invention relates generally to a device for removing contaminants, such as tar and nicotine, from the air, and particularly to an intraoral device designed for placement in the mouth of a smoker to absorb at least a portion of the tar and nicotine which would normally be inhaled by the smoker.

BACKGROUND OF THE INVENTION

Various devices for removing contaminants from the air prior to inhalation are currently known. For example, a variety of masks are available which can be placed over the nose and mouth of the wearer to filter various airborne contaminants. Additionally, many brands of cigarettes already include self-contained filters which remove a portion of the tar and nicotine as it is inhaled through the cigarette.

Other devices have been designed for intraoral use. Filter devices have been designed for insertion between the teeth and lips of a wearer to filter the air inhaled by the wearer. Such devices generally include a screen or filter material.

Although some of these devices may work well, they are awkward and impractical to use on a day-to-day basis. For example, if a smoker wishes to remove a greater amount of the tar and nicotine from the smoke inhaled, it would be inconvenient to wear a mask or filter device covering the entire opening of the smoker's mouth. Additionally, such conventional filter devices are readily seen and unsightly in appearance.

Another disadvantage of existing devices is their failure to remove or cover the bad odors of many contaminants, such as the tar or nicotine in cigarette smoke. It would be beneficial to have an intraoral device convenient to use and not visible to common observers, yet able to remove at least a portion of the airborne contaminants.

The present invention addresses the drawbacks of current personal filter devices, particularly intraoral filter devices.

SUMMARY OF THE INVENTION

The present invention features an intraoral device for absorbing airborne contaminants, such as tar and nicotine normally inhaled or ingested by a smoker. The intraoral device comprises a generally flexible pad configured for insertion into the mouth of a wearer. The pad is configured to lie longitudinally within the mouth of the wearer to absorb airborne contaminants without obstructing the intake of substance through the wearer's mouth.

According to another aspect of the invention, the intraoral device is specifically designed to absorb tar and nicotine. In this embodiment, a flexible pad is configured to lie along the palate of a wearer. A plurality of tar and nicotine absorbent particles are embedded into the flexible pad. Additionally, a retainer portion is attached to the flexible pad to engage a tooth of the wearer to secure the flexible pad in proximity to the wearer's palate.

According to another aspect of the invention, a method is presented for removal of contaminants from air prior to the air entering that individual's lungs. The method includes the steps of forming a flexible pad configured for insertion into a wearer's mouth and embedding contaminant absorbent material into the flexible pad.

According to yet another aspect of the invention, an intraoral device is designed for freshening the breath of a user over a sustained period of time. The intraoral device includes a chewable pad. The device also includes a first flavored bit having an enteric coating of a first general thickness and a second flavored bit having an enteric coating of a second general thickness.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENT

Figure 1:
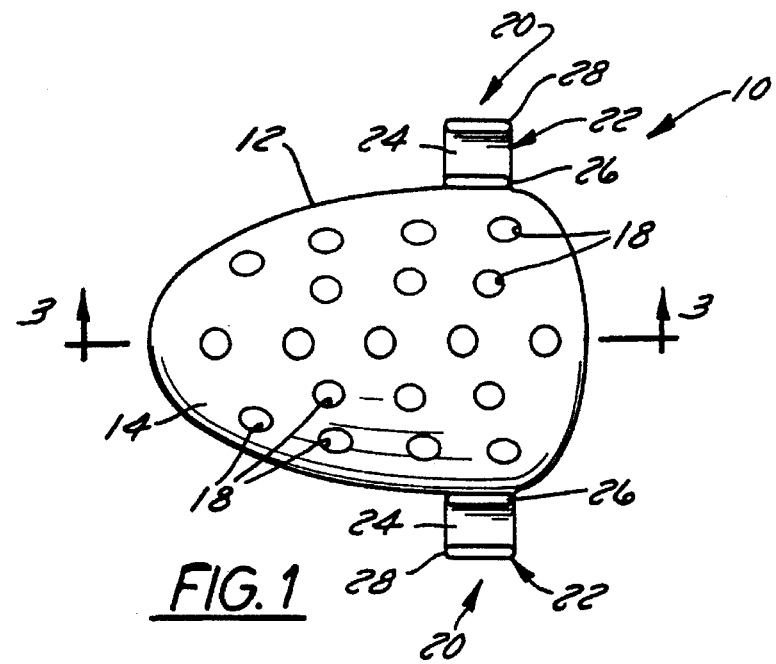
FIG. 1 is a top plan view of an intraoral device according to a preferred form of the present invention.
Figure 2:
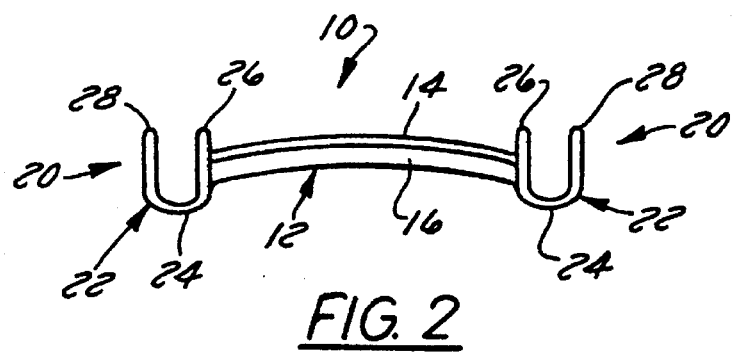
FIG. 2 is a front elevation view of the device shown in FIG. 1.
Figure 3:
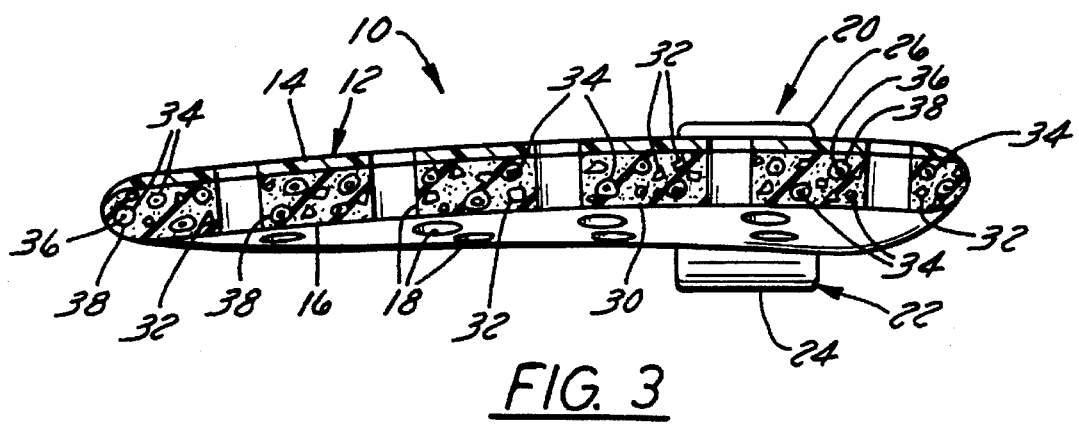
FIG. 3 is a cross sectional view taken generally along line 3—3 of FIG. 1.

A preferred embodiment of an intraoral device 10, according to the present invention, is illustrated in FIGS. 1–3. Intraoral device 10 is designed to fit within the mouth of a wearer and to remove noxious airborne contaminants, such as tar and nicotine. The device may be particularly helpful to smokers who wish to cut down on the amount of tar and nicotine which would otherwise be inhaled into his or her lungs.

Referring generally to FIG. 1, intraoral device 10 includes a flexible pad 12 configured for insertion into the mouth of a wearer. Flexible pad 12 may be designed for insertion into a variety of locations within the wearer's mouth, including disposition between the teeth and cheeks i.e. the buccal vestibule area of the human mouth. However, the pad is preferably configured to lie generally longitudinally along the roof of the mouth. Thus, as smoke or other contaminants are breathed into the mouth, flexible pad 12 is positioned to absorb at least some of the passing airborne contaminants.

Pad 12 preferably includes an upper layer 14 (see FIG. 2) which engages or lies along the palate of the wearer. Upper layer 14 is generally a non-absorbing material, such as a non absorbing plastic, to prevent prolonged contact between the contaminants absorbed by flexible pad 12 and the surface of the wearer's mouth. Pad 12 also includes a lower layer 16 which preferably lies adjacent upper layer 14 and is attached to upper layer 14. Lower layer 16 is the layer exposed to the airborne contaminants to absorb at least certain of the airborne contaminants.

A plurality of fenestrations 18 extend through flexible pad 12 in a generally transverse direction to layers 14 and 16 and allow air flow therethrough. Fenestrations 18 may be pores or openings as shown in FIG. 1 and are designed to allow air flow therethrough in case intraoral device 10 becomes dislodged and positioned in the throat of the wearer.

Optionally, intraoral device 10 includes a retainer portion 20 attached to flexible pad 12. Retainer portion 20 may have various configurations to hold flexible pad 12 between the wearer's teeth, along side the wearer's teeth, or over the wearer's teeth. In the illustrated embodiment, retainer portion 20 includes two extensions 22 designed to fit over the wearer's molar teeth and to hold pad 12 along the wearer's palate. Each extension 22 includes a base 24, an inner tab 26, and an outer tab 28. Inner tab 26 and outer tab 28 cooperate to grip a tooth or a plurality of teeth of the wearer. This securely holds device 10 in the desired location while remaining virtually unnoticeable to other persons interacting with the wearer.

As illustrated generally in FIG. 3, flexible pad 12 is designed to absorb airborne contaminants, e.g. tar and nicotine. In a preferred embodiment, lower layer 16 is a foam rubber layer 30 impregnated with a contaminant absorbent material 32, such as activated charcoal particles. The foam rubber material 30 is sufficiently porus to allow absorption of contaminants by the activated charcoal throughout lower layer 16.

Flexible pad 12 may also be at least partially impregnated with a breath freshening substance 34. Breath freshening substance 34 can include liquid, crystals, or vapors contained within the foam rubber material 30. In the illustrated embodiment, the breath freshening substance 34 is in the form of flavor crystals having flavored bits 36 encapsulated by enteric coatings 38. Some of the breath freshening crystals omit enteric coating 38 to provide instantaneous freshening once intraoral device 10 is placed in the wearer's mouth. Other flavor crystals 36 are encapsulated by enteric coatings 38 are be dissolved by the saliva of the wearer to provide a later release of breath freshener. By encapsulating flavor crystals 36 with enteric coatings of different thicknesses, the release of breath freshener is maintained over a longer period of time.

For example, a first group of flavored crystals 36 may have relatively thin enteric coatings. A second group of the flavored crystals may have enteric coatings which are somewhat thicker than those of the first group. A third group of flavored crystals may be coated with a still thicker enteric coating to provide multiple groups of flavor crystals to release flavor and/or breath freshener at different times. Generally, when the flavor crystals are used up, the tar and nicotine absorbing particles 32 of pad 12 will be at least partially saturated and the device can then be disposed of.

It will be understood that the foregoing description is of preferred exemplary embodiments of this invention and that the invention is not limited to the specific forms shown. For example, intraoral device 10 may have a variety of configurations to accommodate insertion into various regions of the wearer's mouth. A variety of plastic, rubber, or other materials acceptable for intraoral placement may be used to construct the intraoral device. Similarly, a variety of contaminant absorbent materials or breadth freshening substances can be interchanged. Similarly, flexible pad 12 may be made from a variety of materials including chewing gums or other pliable materials. These and other modifications may be made in the design and arrangement of the elements without departing from the scope of the invention as expressed in the appended claims.

I claim:

1. A disposable intraoral device for absorbing airborne contaminants normally inhaled into the lungs of a wearer, comprising:

a pad conformed to fit the palate of a human mouth, the pad including:
an airborne contaminant absorber;
a first surface configured to lie along the palate of a human mouth; and
an exterior absorbent surface exposed to the tongue of a human mouth.

2. The intraoral device of claim 1, wherein the pad is a flexible pad and includes an upper layer partially bounded by the first surface configured to engage the palate of a wearer and a lower layer generally opposite the upper layer and partially bounded by the exterior absorbent surface, the upper layer including a non-absorbing material and the lower layer including a tar and nicotine absorbing material.

3. The intraoral device of claim 2, wherein the flexible pad is at least partially impregnated with a breath freshening substance.

4. The intraoral device of claim 3, wherein the flexible pad includes activated charcoal embedded therein.

5. A disposable intraoral device for absorbing airborne contaminants normally inhaled into the lungs of a wearer, comprising:

a pad conformed to fit the palate of a human mouth, the pad including an airborne contaminant absorber;
wherein the pad is a flexible pad and includes an upper layer configured to engage the palate of a wearer and a lower layer generally opposite the upper layer, the upper layer including a non-absorbing material and the lower layer including a tar and nicotine absorbing material;
the flexible pad being at least partially impregnated with a breath freshening substance and including activated charcoal embedded therein;
wherein the breath freshening substance includes flavor crystals having enteric coatings of varying thicknesses to provide a controlled release of breath freshener.

6. The intraoral device of claim 5, wherein the flexible pad includes a plurality of fenestrations.

7. The intraoral device of claim 6, wherein the plurality of fenestrations permit sufficient airflow therethrough to permit a wearer to breathe even if the flexible pad becomes lodged in the throat of a wearer.

8. The intraoral device of claim 7, further comprising a retainer portion extended from the flexible pad, the retainer portion being sized to cooperate with the teeth of a wearer, thereby holding the flexible pad generally along the palate of a wearer.

9. The intraoral device of claim 8, wherein the retaining portion includes a pair of clips configured to fit over a plurality of molar teeth of a wearer.

10. An intraoral device for absorbing tar and nicotine normally inhaled by a smoker, comprising:

a flexible pad configured to lie along the palate of a wearer, the flexible pad including an exterior absorbent surface disposed within the mouth of a wearer;
a plurality of tar and nicotine absorbent particles embedded in the flexible pad; and
a retainer portion attached to the flexible pad, the retainer portion engaging a tooth of a wearer to secure the flexible pad generally along the palate.

11. An intraoral device for absorbing tar and nicotine normally inhaled by a smoker, comprising:

a flexible pad configured to lie along the palate of a wearer;
a plurality of tar and nicotine absorbent particles embedded in the flexible pad;
a retainer portion attached to the flexible pad, the retainer portion engaging a tooth of a wearer to secure the flexible pad generally along the palate; and
further comprising a plurality of breath freshening flavor crystals, wherein at least some of the breath freshening flavor crystals have enteric coatings.

12. The intraoral device of claim 11, wherein the tar and nicotine absorbent particles include activated charcoal.

13. The intraoral device of claim 12, wherein the flexible pad includes a tar and nicotine absorbent surface and a nonabsorbent surface opposite the absorbent surface, the nonabsorbent surface being configured to lie along the palate of a wearer.

14. The intraoral device of claim 13, wherein the pad includes pores which allow the passage of air therethrough.

15. A method for removing contaminants from inhaled air prior to the air entering the lungs, the method comprising the steps of:

forming a flexible pad configured for insertion into a wearer's mouth;

shaping at least one surface of the flexible pad to lie along the palate a wearer;

embedding contaminant absorbent material into the flexible pad; and bounding the contaminant absorbent material by a single absorbent surface exposed to the tongue of a wearer's mouth.

16. The method for removing contaminants of claim 15, further comprising the step of impregnating the flexible pad with a flavored substance.

17. The method for removing contaminants of claim 15, further comprising the step of placing the flexible pad into the mouth of a wearer.

18. The method for removing contaminants of claim 15, further comprising the step of:

connecting a retainer to the flexible pad to facilitate retention of the flexible pad along the palate of a wearer.

19. A method for removing contaminants from inhaled air prior to the air entering the lungs, the method comprising the steps of:

forming a flexible pad configured for insertion into a wearer's mouth;

shaping at least one surface of the flexible pad to lie along the palate of a wearer;

embedding contaminant absorbent material into the flexible pad; and further comprising the step of impregnating the flexible pad with a plurality of breath freshening flavor crystals having enteric coatings.

20. A disposable intraoral device for absorbing airborne contaminants normally inhaled into the lungs of a wearer, comprising:

a pad conformed to fit the buccal vestibule of a human mouth, the pad including an airborne contaminant absorber;

a first surface configured to lie along the palate of a human mouth; and an exterior absorbent surface exposed to the tongue of a human mouth.

* * * * *